United States Patent
Kusuda et al.

(10) Patent No.: US 9,273,329 B2
(45) Date of Patent: Mar. 1, 2016

(54) METHOD FOR PRODUCING ETHANOL USING CELLULOSIC BIOMASS AS RAW MATERIAL

(71) Applicant: KAWASAKI JUKOGYO KABUSHIKI KAISHA, Kobe-shi, Hyogo (JP)

(72) Inventors: Hiromasa Kusuda, Kobe (JP); Noriaki Izumi, Kobe (JP); Hironori Tajiri, Kobe (JP); Shoji Tsujita, Itami (JP); Takashi Nishino, Suita (JP); Manabu Masamoto, Kobe (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 155 days.

(21) Appl. No.: 14/346,709

(22) PCT Filed: Sep. 24, 2012

(86) PCT No.: PCT/JP2012/006050
§ 371 (c)(1),
(2) Date: Mar. 21, 2014

(87) PCT Pub. No.: WO2013/046624
PCT Pub. Date: Apr. 4, 2013

(65) Prior Publication Data
US 2014/0234936 A1    Aug. 21, 2014

(30) Foreign Application Priority Data

Sep. 30, 2011 (JP) ................................ 2011-218036

(51) Int. Cl.
*C12P 7/10* (2006.01)

(52) U.S. Cl.
CPC .............. *C12P 7/10* (2013.01); *C12P 2201/00* (2013.01); *C12P 2203/00* (2013.01); *Y02E 50/16* (2013.01)

(58) Field of Classification Search
None
See application file for complete search history.

(56) References Cited

U.S. PATENT DOCUMENTS 3,212,933 A * 10/1965 Hess ................... D21C 11/0007
 127/37
7,718,070 B2 * 5/2010 Mahnon ............... B01D 15/363
 127/46.2

FOREIGN PATENT DOCUMENTS

| JP | 2000-186102 A | 7/2000 |
|---|---|---|
| JP | 2002-059118 A | 2/2002 |
| JP | 2003-212888 A | 7/2003 |
| JP | 2006-075007 A | 3/2006 |
| JP | 2008-43229 | 2/2008 |
| JP | 2009-022239 A | 2/2009 |
| JP | 2009-195189 A | 9/2009 |
| JP | 2010-166831 A | 8/2010 |
| JP | 2010-253348 A | 11/2010 |
| JP | 2010-279255 A | 12/2010 |
| JP | 2011-032388 A | 2/2011 |

OTHER PUBLICATIONS

English Translation of JP 2010279255, Sep. 2015, 47 pgs.*
International Search Report for PCT/JP2012/006050, mailed Nov. 6, 2012, 2 pgs.
Office Action for Chinese Patent Application No. 20128004104.6, dated Dec. 25, 2014, 8 pgs.
Dong et al., "Using trifluoroacetic acid to pretreat lignocellulosic biomass", Biomass and Bioenergy 33:1719-1723 (2009).

* cited by examiner

*Primary Examiner* — Thane Underdahl
(74) *Attorney, Agent, or Firm* — Marshall, Gerstein & Borun LLP

(57) ABSTRACT

In the present disclosure, after a volatile organic acid is added as a catalyst to a slurry and the hydrolytic saccharification reaction of hemicellulose is performed, the volatile organic acid (including one added to the slurry and one produced as a by-product) contained in a C5 saccharified solution can be easily recovered by adding a small amount of sulfuric acid to the C5 saccharified solution and subjecting the C5 saccharified solution to air stripping treatment. The efficiency of hydrolytic saccharification of hemicellulose into C5 sugars using a volatile organic acid can also be continuously improved by adding the recovered volatile organic acid as a catalyst to another slurry of cellulosic biomass.

5 Claims, 2 Drawing Sheets

METHOD FOR PRODUCING ETHANOL USING CELLULOSIC BIOMASS AS RAW MATERIAL

TECHNICAL FIELD

The present invention relates to a method for producing ethanol (bioethanol) by alcoholic fermentation of sugars produced by hydrolyzing cellulosic biomass in a supercritical or subcritical state, in which a volatile organic acid is used as a catalyst for hydrolysis reaction and is recovered and reused.

BACKGROUND ART

As part of utilizing biomass energy, attempts have been made to decompose cellulose or hemicellulose as main components of plants to obtain ethanol. The thus obtained ethanol is planned to be mainly used as fuel such as part of automotive fuel or a gasoline alternative.

The main components of plants include cellulose (a polymer of glucose as a C6 sugar containing 6 carbon atoms), hemicellulose (a polymer of a C5 sugar containing 5 carbon atoms and a C6 sugar), lignin, and starch. Ethanol is produced by fermentation action of microorganisms, such as yeast, using, as a raw material, sugars such as C5 sugars, C6 sugars, and oligosaccharides as complexes of them.

The industrial use of the following three methods is being contemplated to decompose cellulosic biomass such as cellulose or hemicellulose into sugars: 1) a hydrolysis method utilizing the oxidation power of a strong acid such as sulfuric acid; 2) an enzymatic decomposition method; and 3) a method utilizing the oxidation power of supercritical water or subcritical water. However, it is difficult to practically use the acid decomposition method 1) from an economical viewpoint. This is because an added acid acts as an inhibitor of yeast fermentation, and therefore absolutely needs to be neutralized after decomposition of cellulose or hemicellulose into sugars and before alcoholic fermentation of the sugars, and the neutralization treatment is costly. The enzymatic decomposition method 2) can be performed at ordinary temperature and constant pressure, but no effective enzyme has been found. Even if an effective enzyme is found, it is expected that the production cost of the enzyme will be expensive. Therefore, from an economical viewpoint, there seems to be no prospect for actually using the enzymatic decomposition method on an industrial scale.

PTL 1 discloses, as the method 3) for hydrolyzing cellulosic biomass into sugars with supercritical water or subcritical water, a method for producing a water-insoluble polysaccharide by bringing a cellulose powder into contact with pressurized hot water at 240 to 340° C. to hydrolyze cellulose. PTL 2 discloses a method in which biomass cut into small pieces is hydrolyzed with hot water pressurized to a saturated water vapor pressure or higher at 140 to 230° C. for a predetermined time to decompose/extract hemicellulose, and is then hydrolyzed with pressurized hot water heated to a decomposition temperature of cellulose or higher to decompose/extract cellulose. PTL 3 discloses a method for producing glucose and/or a water-soluble cello-oligosaccharide, in which cellulose having an average degree of polymerization of 100 or higher is subjected to a contact reaction with supercritical water or subcritical water at a temperature of 250° C. or higher but 450° C. or lower and a pressure of 15 MPa or higher but 450 MPa or lower for 0.01 second or longer but 5 seconds or shorter, and is then cooled and hydrolyzed by contact with subcritical water at a temperature of 250° C. or higher but 350° C. or lower and a pressure of 15 MPa or higher but 450 MPa or lower for 1 second or longer but 10 minutes or shorter.

PTL 4 discloses a method for inexpensively and easily producing sugars using a wood-based plant as a raw material while reducing the amounts of energy and water to be used for hydrolyzing polysaccharides, in which treatment water for use in hydrolysis treatment contains acidic water obtained after sugars are recovered from a sugar-containing hydrolysis extract obtained by hydrolysis treatment of the wood-based plant. According to PTL 4, the pH of the treatment water for use in hydrolysis is preferably 2.6 to 2.9.

PTL 5 discloses a sugar production method in which polysaccharides are decomposed by a hydrothermal reaction in hot water containing an organic acid such as formic acid, acetic acid, or oxalic acid at a temperature of 120 to 300° C. and a pressure of 0.2 to 100 MPa. PTL 5 discloses that the decomposition time of polysaccharides can be reduced by adding an organic acid.

PTL 6 discloses a lignocellulose pretreatment method in which lignocellulosic biomass is hydrolyzed in dilute sulfuric acid at 140 to 220° C. for 3 to 20 minutes, the hydrolysate is then subjected to solid-liquid separation and thus separated into a primary saccharified solution and a solid (dewatered cake), the solid is mixed with hydrated lime and heated at 90 to 150° C. for to 120 minutes, and the lime-treated solid is then enzymatically hydrolyzed using cellulase to obtain a secondary saccharified solution. PTL 6 also discloses that a hydrated lime-containing liquid separated by subjecting the solid after lime treatment to solid-liquid separation is used for neutralization of the primary saccharified solution containing dilute sulfuric acid.

CITATION LIST

Patent Literatures

PTL 1: Japanese Laid-Open Patent Application Publication No. 2000-186102
PTL 2: Japanese Laid-Open Patent Application Publication No. 2002-59118
PTL 3: Japanese Laid-Open Patent Application Publication No. 2003-212888
PTL 4: Japanese Laid-Open Patent Application Publication No. 2008-43229
PTL 5: Japanese Laid-Open Patent Application Publication No. 2009-195189
PTL 6: Japanese Laid-Open Patent Application Publication No. 2006-75007

SUMMARY OF INVENTION

Technical Problem

The method for saccharifying/decomposing (hydrolyzing) cellulose or hemicellulose as a main component of biomass with high-temperature and high-pressure supercritical water or subcritical water does not need acid neutralization treatment and is therefore smaller in treatment cost and more environmentally friendly than the hydrolysis method using a strong acid. However, as disclosed in PTL 6, it is known that, also in the case of the method for hydrolyzing cellulose or hemicellulose with supercritical water or subcritical water, the efficiency of saccharification is improved by adding dilute sulfuric acid as a catalyst to a slurry.

The method disclosed in PTL 6 achieves high saccharification efficiency, but tends to be high in the treatment cost of the entire process due to the costs of sulfuric acid as a catalyst and lime as a neutralizer, because the total amount of sulfuric acid added is neutralized with lime.

An object of the present invention is to provide a method for producing ethanol using cellulosic biomass as a raw material, in which hemicellulose is saccharified/decomposed by utilizing a volatile organic acid as a catalyst, and then the volatile organic acid is recovered from a C5 saccharified solution and reused as a catalyst for hydrolytic saccharification of hemicellulose to reduce treatment cost.

Solution to Problem

In order to achieve the above object, the present inventors have intensively studied, and as a result, have found that after a volatile organic acid is added as a catalyst to a slurry and the hydrolytic saccharification reaction of hemicellulose is performed, the volatile organic acid (including one added to the slurry and one produced as a by-product) contained in a C5 saccharified solution can be easily recovered by adding a small amount of sulfuric acid to the C5 saccharified solution and subjecting the C5 saccharified solution to air stripping treatment. Further, the present inventors have also found that the efficiency of hydrolytic saccharification of hemicellulose into C5 sugars using a volatile organic acid can be continuously improved by adding the recovered volatile organic acids as a catalyst to another slurry of cellulosic biomass. These findings have led to the completion of the present invention.

More specifically, the present invention provides a method for producing ethanol using cellulosic biomass as a raw material, characterized by including:

a first hydrolytic saccharification step of adding a volatile organic acid to a slurry of cellulosic biomass and hydrothermally treating the slurry in a supercritical or subcritical state to saccharify/decompose hemicellulose contained in the cellulosic biomass into C5 sugars;

a first solid-liquid separation step of subjecting the slurry after the first hydrolytic saccharification step to solid-liquid separation;

a recovery step of adding sulfuric acid to a C5 saccharified solution obtained in the first solid-liquid separation step, and then subjecting the C5 saccharified solution to air stripping treatment or distillation treatment to recover the volatile organic acid contained in the C5 saccharified solution;

a second hydrolytic saccharification step of slurrying a dewatered cake obtained in the first solid-liquid separation step by adding water and hydrothermally treating the slurry in a supercritical or subcritical state to saccharify/decompose cellulose contained in the cellulosic biomass into C6 sugars;

a second solid-liquid separation step of subjecting the slurry after the second hydrolytic saccharification step to solid-liquid separation;

a fermentation step of subjecting the C5 saccharified solution after the recovery step and a C6 saccharified solution obtained in the second solid-liquid separation step to alcoholic fermentation; and a distillation step of distilling a fermented liquid obtained in the fermentation step to concentrate ethanol, wherein the volatile organic acid recovered in the recovery step is reused as all or part of the volatile organic acid to be added to the slurry in the first hydrolytic saccharification step.

In the ethanol production method according to the present invention, first, the first hydrolytic saccharification step is performed in which a volatile organic acid is added to a slurry of cellulosic biomass and the slurry is hydrothermally treated in a supercritical or subcritical state, and then sulfuric acid is added to a C5 saccharified solution to reduce its pH. Then, the volatile organic acid (including one added to the slurry and one produced as a by-product) contained in the C5 saccharified solution is recovered by subjecting the C5 saccharified solution to air stripping treatment. The volatile organic acid contained in the C5 saccharified solution is a water-soluble weak acid, and therefore can be easily recovered from the C5 saccharified solution by adding sulfuric acid, which is a non-volatile strong acid, to the C5 saccharified solution to reduce its pH and then subjecting the C5 saccharified solution to air stripping treatment. The air stripping treatment is more energy-saving as compared to a distillation method, and uses a small amount of sulfuric acid and is therefore lower in the cost of recovery as compared to a recovery method using sulfuric acid as a catalyst and zeolite.

The recovered volatile organic acid is added to the slurry in the subsequent first hydrolytic saccharification step to be separately performed. In such a case where a volatile organic acid is reused as a catalyst, the efficiency of hydrolytic saccharification is lower as compared to a case where sulfuric acid is added, but the total cost for hydrolytic saccharification of hemicellulose into C5 sugars is lower as compared to the case where sulfuric acid is added, because the volatile organic acid can be used as effectively as possible and the cost for acid recovery is also low.

Specific examples of the "volatile organic acid" used in the present invention include formic acid, acetic acid, and lactic acid.

A dewatered cake (solid) obtained in the first solid-liquid separation step is slurried by adding water and hydrothermally treated in a supercritical or subcritical state in the second hydrolytic saccharification step so that cellulose contained in the cellulosic biomass is saccharified/decomposed into C6 sugars. The slurry after the second hydrolytic saccharification step is subjected to solid-liquid separation in the second solid-liquid separation step and thus separated into a dewatered cake and a C6 saccharified solution.

It is preferred that in the first hydrolytic saccharification step, the volatile organic acid is added to the slurry in a concentration of 0.1% by mass or higher but 10% by mass or lower.

In order to allow the volatile organic acid to effectively function as a catalyst in the first hydrolytic saccharification step, the concentration of the volatile organic acid in the slurry of cellulosic biomass is preferably 0.1% by mass or higher. On the other hand, if the concentration of the volatile organic acid exceeds 10% by mass, a problem arises in which the efficiency of hydrolytic saccharification cannot be expected to be further improved, because it is difficult to make the pH lower even when the concentration of the volatile organic acid is made higher than 10% by mass.

When, in the first hydrolytic saccharification step, the consumption of the volatile organic acid added to the slurry is large and the amount of the volatile organic acid produced as a by-product is small, the concentration of the volatile organic acid in the saccharified solution is low, and therefore the amount of the volatile organic acid to be recovered is also small. Therefore, even if all the volatile organic acid recovered from the saccharified solution is added to the slurry of cellulosic biomass, the concentration of the volatile organic acid in the slurry cannot be adjusted to 0.1% by mass or higher but 10% by mass or lower.

In such a case, it is therefore preferred that all the volatile organic acid recovered from the saccharified solution is reused as the volatile organic acid to be added to the slurry in the first hydrolytic saccharification step and the volatile organic acid is added to the slurry from the outside of a reaction system so that the concentration of the volatile organic acid (total concentration of the recovered volatile organic acid and the volatile organic acid supplied from the outside of the reaction system) in the slurry is adjusted to 0.1% by mass or higher but 10% by mass or lower. The volatile organic acid added to the slurry is recovered from the saccharified solution and reused, and therefore the amount of the volatile organic acid that should be added from the outside of the reaction system corresponds to the amount of the volatile organic acid consumed in the hydrolytic saccharification step and is therefore small.

On the other hand, when, in the first hydrolytic saccharification step, the consumption of the volatile organic acid added to the slurry is small and the amount of the volatile organic acid produced as a by-product is large, the concentration of the volatile organic acid in the saccharified solution is high, and therefore the amount of the volatile organic acid to be recovered is also large. In such a case, the concentration of the volatile organic acid in the slurry can be adjusted to 0.1% by mass or higher but 10% by mass or lower by adding part of the volatile organic acid recovered from the saccharified solution to the slurry of cellulosic biomass.

It is preferred that the method further includes a third solid-liquid separation step of adding lime to the C5 saccharified solution after the recovery step, and separating the resulting gypsum by solid-liquid separation to remove the sulfuric acid and a fermentation inhibitor contained in the C5 saccharified solution.

In the recovery step, a small amount of sulfuric acid that is a strong acid is added to the C5 saccharified solution, and therefore, the saccharified solution cannot be directly transferred to the fermentation step. Therefore, lime is added to the C5 saccharified solution to neutralize the sulfuric acid remaining in the C5 saccharified solution, and precipitated gypsum is separated by solid-liquid separation, which makes it possible to effectively remove the sulfuric acid contained in the C5 saccharified solution.

In the present invention, sulfuric acid is used in the recovery step, but unlike the technique disclosed in PTL 6, the amount of sulfuric acid to be used is small because sulfuric acid is used for the purpose of liberating the volatile organic acid. Therefore, the amount of lime for use in neutralization is also small, and the cost for neutralizing sulfuric acid is low. Further, the amount of gypsum formed is also small, and therefore gypsum is easily removed from the saccharified solution.

It is to be noted that the C5 saccharified solution contains, in addition to the volatile organic acid, by-products that are over-decomposition products of C5 sugars, such as furfural and hydroxymethylfurfural. These by-products also inhibit alcoholic fermentation, but are adsorbed to gypsum when lime is added to the C5 saccharified solution. Therefore, these by-products can be removed concurrently with the removal of gypsum from the C5 saccharified solution by solid-liquid separation.

It is preferred that the third solid-liquid separation step is a solid-liquid separation step in which gypsum is separated by solid-liquid separation using a thickener or a settling tank.

It is preferred that the C5 saccharified solution (supernatant in the settling tank) from which gypsum has been removed in the third solid-liquid separation step is concentrated by a reverse osmosis membrane device.

The foregoing objects, other objects, characteristics, and advantages of the present invention will be made clear from the detailed description of preferred embodiments given below with reference to the attached drawings.

Advantageous Effects of Invention

According to the present invention, a volatile organic acid as a catalyst is repeatedly used for hydrolytic saccharification of cellulosic biomass into C5 sugars, and therefore the efficiency of hydrolytic saccharification into C5 sugars can be improved while the total cost for alcohol production is saved.

DESCRIPTION OF EMBODIMENTS

Hereinbelow, embodiments of the present invention will be described with appropriate reference to the drawings. The present invention is not limited to the description given below.

Embodiment 1

Figure 1:
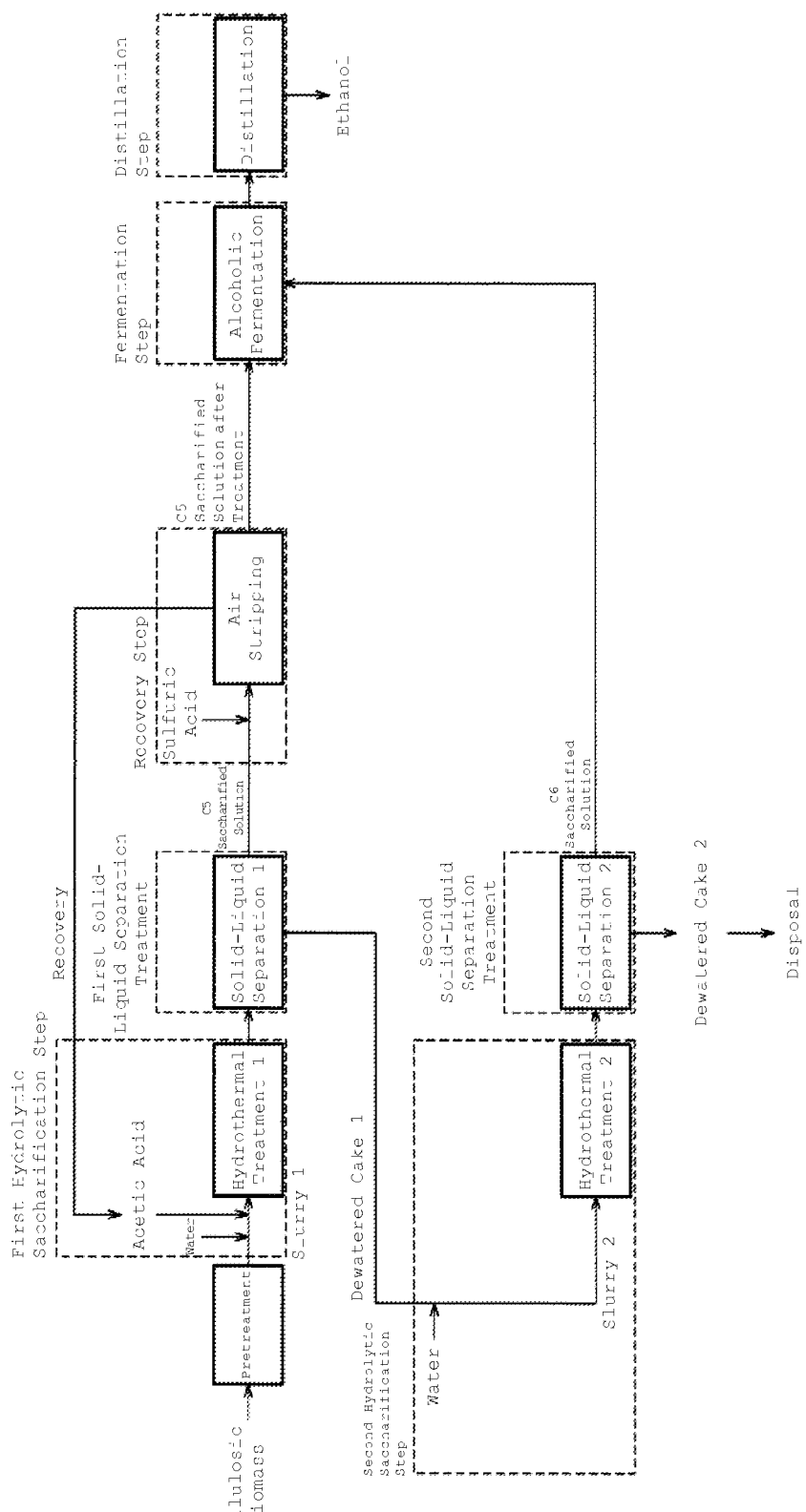
FIG. 1 shows a schematic flow chart illustrating Embodiment 1 of the present invention.

FIG. 1 shows a schematic flow chart illustrating Embodiment 1 of the present invention. Here, a case where acetic acid is added as a volatile organic acid to a slurry will be described.

(Pretreatment Step)

First, as pretreatment, cellulosic biomass (e.g., plant-based biomass such as bagasse, sugar beet pulp, or straws) is crushed into small pieces of several millimeters or less.

(First Hydrolytic Saccharification Step)

The crushed cellulosic biomass is slurried by adding water and acetic acid with stirring. The amount of water contained in a slurry 1 is preferably adjusted to 1% by mass or higher but 50% by mass or lower. Further, the concentration of acetic acid in the slurry 1 is preferably adjusted to 0.1% by mass or higher but 10% by mass or lower.

The slurry 1 containing acetic acid is preheated, if necessary, and is then supplied into a pressure vessel. A specific example of the pressure vessel is an indirect heating-type pressure vessel. In the pressure vessel, the slurry 1 is hydrothermally treated at a temperature of 140° C. or higher but 200° C. or lower and a pressure of 1 MPa or higher but 5 MPa of lower (hydrothermal treatment 1). Hemicellulose in the cellulosic biomass is saccharified/decomposed (hydrolyzed) into C5 sugars by this hydrothermal treatment. At this time, the efficiency of hydrolytic saccharification is improved due to the catalytic action of acetic acid as compared to a case where acetic acid is not added.

After the hydrothermal treatment is performed for a certain period of time, the pressure and temperature in the pressure vessel are reduced, and then the slurry 1 is taken out. At this time, the slurry 1 is preferably supplied from the pressure vessel to a flash tank and quenched to a subcritical temperature or lower by flash evaporation.

(First Solid-Liquid Separation Step)

Then, the slurry 1 after the first hydrolytic saccharification step is supplied to a solid-liquid separation device and separated into a C5 saccharified solution and a dewatered cake 1 (solid) by solid-liquid separation (solid-liquid separation 1).

(Recovery Step)

Then, sulfuric acid is added to the C5 saccharified solution after the first solid-liquid separation step. The amount of sulfuric acid to be added is increased or decreased depending on the concentration of acetic acid in the C5 saccharified solution. The sulfuric acid-containing C5 saccharified solution is supplied to an air stripping device such as a packed tower. In the air stripping device, acetic acid is recovered by a condenser. The recovered acetic acid is added to the slurry and reused as a catalyst in the subsequent first hydrolytic saccharification step to be separately performed.

A determination as to whether the total amount of the recovered acetic acid is added to the slurry or part of the recovered acetic acid is added to the slurry is made based on the concentration and amount of the recovered acetic acid. In a case where the concentration of the volatile organic acid in the slurry cannot be adjusted to 0.1% by mass or higher but 10% by mass or lower even when the total amount of the recovered acetic acid is added to the slurry, acetic acid is added from the outside of a reaction system so that the total concentration of acetic acid (total concentration of the recovered acetic acid and acetic acid added from the outside of the reaction system) is adjusted to 0.1% by mass or higher but 10% by mass or lower.

On the other hand, the C5 saccharified solution after air stripping treatment is supplied to a subsequent fermentation step. At this time, an alkaline agent such as caustic soda or hydrated lime is preferably added to the C5 saccharified solution to neutralize the sulfuric acid added in the recovery step so that the pH of the saccharified solution is adjusted to a value that does not affect the fermentation step.

(Second Hydrolytic Saccharification/Decomposition Step)

The dewatered cake 1 is slurried by adding water, and a resulting slurry 2 is supplied to a pressure vessel. The amount of water contained in the slurry 2 is preferably adjusted to 1% by mass or higher but 50% by mass or lower. The slurry 2 is hydrothermally treated at a temperature of 240° C. or higher but 300° C. or lower and a pressure of 4 MPa or higher but 30 MPa or lower in the same manner as in the hydrothermal treatment 1 (hydrothermal treatment 2). Cellulose in the cellulosic biomass is hydrolyzed into C6 sugars by the hydrothermal treatment 2.

After the hydrothermal treatment 2 is performed for a certain period of time, the pressure and temperature in the pressure vessel are reduced, and then the slurry 2 is taken out. At this time, the slurry 2 is preferably supplied from the pressure vessel to a flash tank and quenched to a subcritical temperature or lower by flash evaporation.

(Second Solid-Liquid Separation Step)

The slurry after the second hydrolytic saccharification step is supplied to a solid-liquid separation device and separated into a C6 saccharified solution and a dewatered cake 2 by solid-liquid separation (solid-liquid separation 2) in the same manner as in the first solid-liquid separation step. The C6 saccharified solution is supplied to a subsequent fermentation step. On the other hand, the dewatered cake 2 is appropriately taken out of the system and disposed of.

(Fermentation Step)

The C5 saccharified solution after air stripping treatment and the C6 saccharified solution are subjected to a fermentation step. The fermentation step can be performed using a publicly known fermentation method. In the fermentation step, C5 sugars and C6 sugars contained in the saccharified solution are converted to ethanol. The fermentation step can be performed using a fermentation method publicly known in the field of brewing.

(Distillation Step)

An alcohol-fermented liquid obtained in the fermentation step is distilled to concentrate ethanol. A distillate obtained in the distillation step contains no solid matter and no components other than ethanol. The distillation step can be performed by using a distillation method publicly known as a method for producing distilled liquor.

It is to be noted that in the first hydrolytic saccharification step, volatile organic acids, such as formic acid, derived from the oxidation of C5 sugars are also produced in small amounts as by-products. Such volatile organic acids (including acetic acid produced as a by-product other than acetic acid added to the slurry in the first hydrolytic saccharification step) are also recovered together with acetic acid in the recovery step and used as a catalyst in the first hydrolytic saccharification step. Therefore, when the method according to the present invention is continuously performed, the concentrations of the volatile organic acids other than acetic acid in the recovered acetic acid gradually increase.

Some of the volatile organic acids derived from the oxidation of C5 sugars act as an inhibitor of subsequent alcoholic fermentation. Therefore, acetic acid recovered in the recovery step is preferably periodically disposed of to prevent the accumulation of the volatile organic acids that inhibit alcoholic fermentation within the reaction system.

Embodiment 2

Figure 2:
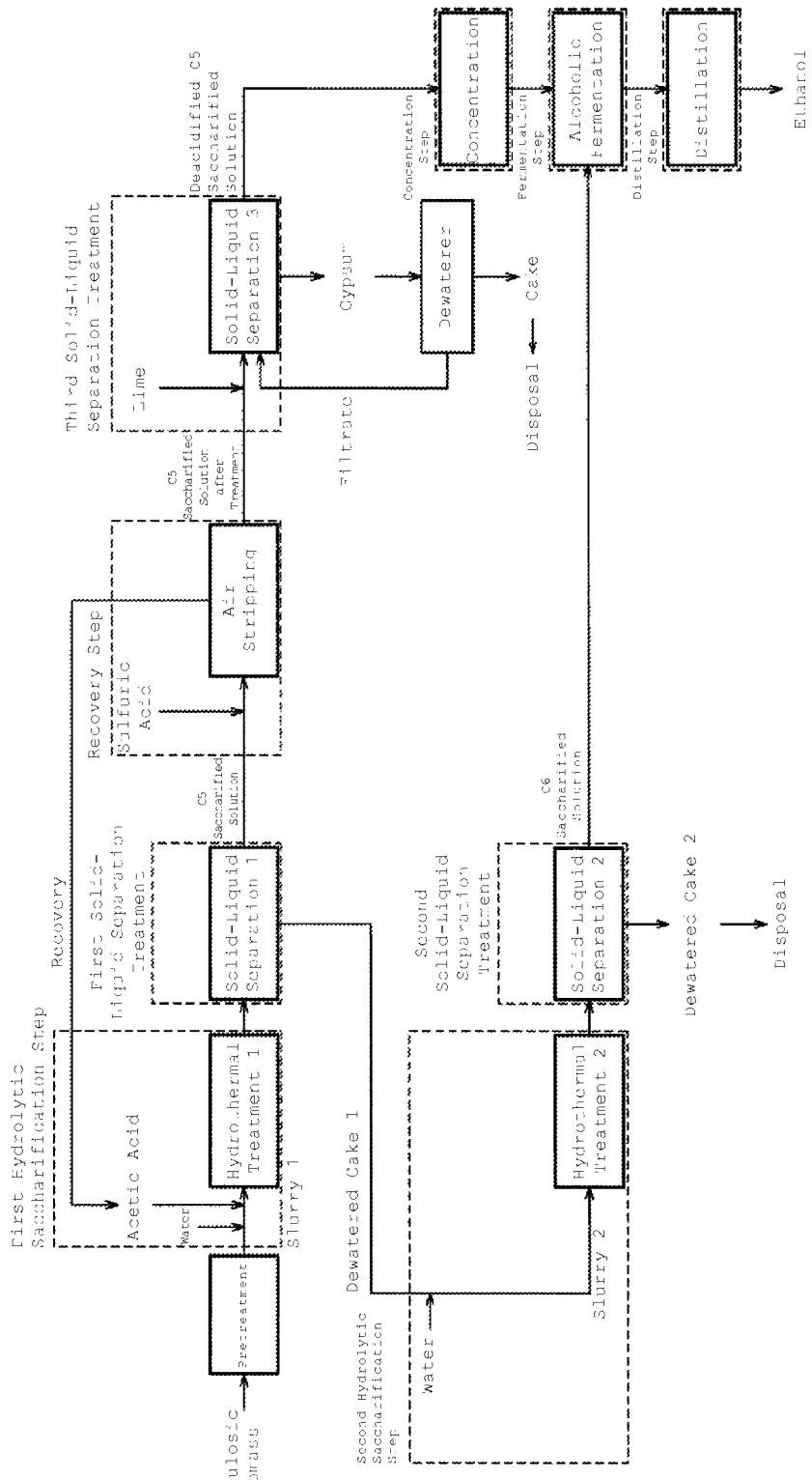
FIG. 2 shows a schematic flow chart illustrating Embodiment 2 of the present invention.

FIG. 2 shows a schematic flow chart illustrating Embodiment 2 of the present invention. The basic flow of this embodiment is the same as that of Embodiment 1, and therefore only the differences from Embodiment 1 will be described here. The same components as in Embodiment 1 are denoted by the same terms as used in Embodiment 1.

(Third Solid-Liquid Separation Step)

In this embodiment, lime is added to the C5 saccharified solution after air stripping treatment. The Sulfuric acid remaining in the C5 saccharified solution is neutralized by adding lime. Gypsum is deposited by the reaction between sulfuric acid and lime, but a by-product such as furfural or hydroxymethylfurfural is adsorbed to the deposited gypsum. The C5 saccharified solution containing lime is separated into the C5 saccharified solution and gypsum by solid-liquid separation (solid-liquid separation 3) using a thickener or a settling tank.

The gypsum is dewatered by a dewaterer, and is appropriately disposed of as a gypsum cake from the solid-liquid separation device. On the other hand, a supernatant in the thickener or settling tank (C5 saccharified solution from which a solid matter has been removed) is supplied to an RO membrane device and concentrated. The efficiency of the fermentation step can be improved by increasing the concentration of sugars in the C5 saccharified solution by concentration.

The C5 saccharified solution after concentration is supplied together with the C6 saccharified solution to the fermentation step. In this embodiment, as described above, the sulfuric acid and a fermentation inhibitor can be easily removed from the C5 saccharified solution after air stripping treatment.

From the foregoing explanations, many improvements and other embodiments of the present invention are apparent to a person skilled in the art. Therefore, the explanations above should be construed as illustrative examples provided for the purpose of teaching a person skilled in the art the best mode for carrying out the present invention. It is possible to substantially alter the details of the structure and/or functions without deviating from the spirit of the present invention.

INDUSTRIAL APPLICABILITY

The ethanol production method according to the present invention is useful in the field of bioenergy as a method for producing ethanol by decomposing cellulosic biomass.

The invention claimed is:

1. A method for producing ethanol using cellulosic biomass as a raw material, comprising:
a first hydrolytic saccharification step of adding a volatile organic acid to a slurry of cellulosic biomass and hydrothermally treating the slurry in a supercritical or subcritical state to saccharify/decompose hemicellulose contained in the cellulosic biomass into C5 sugars;

a first solid-liquid separation step of subjecting the slurry after the first hydrolytic saccharification step to solid-liquid separation;

a recovery step of adding sulfuric acid to a C5 saccharified solution obtained in the first solid-liquid separation step, and then subjecting the C5 saccharified solution to air stripping treatment or distillation treatment to recover the volatile organic acid contained in the C5 saccharified solution;

a second hydrolytic saccharification step of slurrying a dewatered cake obtained in the first solid-liquid separation step by adding water and hydrothermally treating the slurry in a supercritical or subcritical state to saccharify/decompose cellulose contained in the cellulosic biomass into C6 sugars;

a second solid-liquid separation step of subjecting the slurry after the second hydrolytic saccharification step to solid-liquid separation;

a fermentation step of subjecting the C5 saccharified solution after the recovery step and a C6 saccharified solution obtained in the second solid-liquid separation step to alcoholic fermentation; and a distillation step of distilling a fermented liquid obtained in the fermentation step to concentrate ethanol, wherein the volatile organic acid recovered in the recovery step is reused as all or part of the volatile organic acid to be added to the slurry in the first hydrolytic saccharification step.

2. The ethanol production method according to claim 1, wherein in the first hydrolytic saccharification step, the volatile organic acid is added to the slurry in a concentration of 0.1% by mass or higher but 10% by mass or lower.

3. The ethanol production method according to claim 1, further comprising a third solid-liquid separation step of adding lime to the C5 saccharified solution after the recovery step, and separating the resulting gypsum by solid-liquid separation to remove the sulfuric acid and a fermentation inhibitor contained in the C5 saccharified solution.

4. The ethanol production method according to claim 3, wherein the third solid-liquid separation step is a solid-liquid separation step in which the gypsum is separated by solid-liquid separation using a thickener or a settling tank.

5. The ethanol production method according to claim 4, wherein the C5 saccharified solution from which the gypsum has been removed in the third solid-liquid separation step is concentrated by a reverse osmosis membrane device.

* * * * *